US008853405B2

(12) United States Patent
Van Der Schaaf et al.

(10) Patent No.: US 8,853,405 B2
(45) Date of Patent: *Oct. 7, 2014

(54) CRYSTALLINE FORMS OF PITAVASTATIN CALCIUM

(71) Applicant: Nissan Chemical Industries, Ltd., Tokyo (JP)

(72) Inventors: Paul Adriaan Van Der Schaaf, Hagenthal-le-Haut (FR); Fritz Blatter, Reinach (CH); Martin Szelagiewicz, Muenchenstein (CH); Kai-Uwe Schoening, Oberwil (CH)

(73) Assignee: Nissan Chemical Industries Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/016,399

(22) Filed: Sep. 3, 2013

(65) Prior Publication Data

US 2014/0005402 A1    Jan. 2, 2014

Related U.S. Application Data

(63) Continuation of application No. 13/664,498, filed on Oct. 31, 2012, now Pat. No. 8,557,993, which is a continuation of application No. 13/280,431, filed on Oct. 25, 2011, now abandoned, which is a continuation of application No. 12/331,086, filed on Dec. 9, 2008, now abandoned, which is a continuation of application No. 10/544,752, filed as application No. PCT/EP2004/050066 on Feb. 2, 2004, now abandoned.

(30) Foreign Application Priority Data

Feb. 12, 2003    (EP) .................................. 03405080

(51) Int. Cl.
*C07D 215/14*    (2006.01)

(52) U.S. Cl.
CPC .................................. *C07D 215/14* (2013.01)
USPC ....................................................... 546/173

(58) Field of Classification Search
CPC ...................................................... C07D 215/14
USPC ....................................................... 546/173
See application file for complete search history.

(56) References Cited

U.S. PATENT DOCUMENTS

| 3,175,944 | A | 3/1965 | Hoeksema |
|---|---|---|---|
| 5,011,930 | A | 4/1991 | Fujikawa et al. |
| 5,284,953 | A | 2/1994 | Ohara et al. |
| 5,407,929 | A | 4/1995 | Takahashi et al. |
| 5,473,075 | A | 12/1995 | Ohara et al. |
| 5,514,804 | A | 5/1996 | Ohara et al. |
| 5,856,336 | A | 1/1999 | Fujikawa et al. |
| 5,872,130 | A | 2/1999 | Fujikawa et al. |
| 5,939,552 | A | 8/1999 | Ikeda et al. |
| 6,335,449 | B1 | 1/2002 | Ohara et al. |
| 6,528,661 | B2 | 3/2003 | Niddam et al. |
| 6,835,838 | B2 | 12/2004 | Chen et al. |
| 7,371,865 | B2 | 5/2008 | Acemoglu et al. |
| 8,557,993 | B2 * | 10/2013 | Van der Schaaf et al. .... 546/101 |
| 2002/0099224 | A1 | 7/2002 | Niddam et al. |
| 2003/0105359 | A1 | 6/2003 | Van Der Schaaf et al. |
| 2003/0233001 | A1 | 12/2003 | Storz |
| 2004/0063961 | A1 | 4/2004 | Van Der Schaaf et al. |
| 2005/0130978 | A1 | 6/2005 | Yuda et al. |
| 2012/0245200 | A1 | 9/2012 | Ohara et al. |

FOREIGN PATENT DOCUMENTS

| EP | 0 304 063 | 2/1989 |
|---|---|---|
| EP | 0 520 406 | 12/1992 |
| EP | 1 099 694 | 5/2001 |
| EP | 1 472 227 | 11/2004 |
| EP | 1 472 228 | 11/2004 |
| EP | 1 697 326 | 9/2006 |
| JP | 61-171460 | 8/1986 |
| JP | 05-148237 | 5/1993 |
| JP | 6-92970 | 4/1994 |
| JP | 8-12674 | 1/1996 |
| JP | 2005-500382 | 1/2005 |
| JP | 2005-516064 | 6/2005 |
| JP | 2005-520814 | 7/2005 |
| JP | 2007-516952 | 6/2007 |
| WO | 03/016317 | 2/2003 |
| WO | 03/064382 | 8/2003 |
| WO | WO 03/064392 | 8/2003 |
| WO | WO 03/070717 | 8/2003 |
| WO | 03/087091 | 10/2003 |
| WO | WO 2004/072040 | 8/2004 |

OTHER PUBLICATIONS

Information Offer Form dispatched Apr. 6, 2010 in Japanese Patent Application No. 2006-5001997 (with English-language translation).
Information Offer Form dispatched Feb. 23, 2010 in Japanese Patent Application No. 2006-501997 (with English-language translation).
Information Offer Form dispatched Apr. 27, 2010 in Japanese Patent Application No. 2006-501997 (with English-language translation).
Official Action dispatched Jun. 29, 2010 in Japanese Patent Application No. 2006-501997 (with English-language translation).
M. Suzuki et al, First Systematic Chiral Syntheses of Two Pairs of Enantiomers with 3,5-Dihydroxyheptenoic Acid Chain, Associated with a Potent Synthetic Statin NK-104, *Bioorganic & Medicinal Chemistry Letters*, 9 (1999), 2977-2982.
Third Party Observation Submitted on Aug. 21, 2010 in JP 2006-501977 (including excerpt from JP-A-2005-520814).

(Continued)

*Primary Examiner* — D M Seaman
(74) *Attorney, Agent, or Firm* — Oblon, Spivak, McClelland, Maier & Neustadt, L.L.P.

(57) ABSTRACT

The present invention is directed to new crystalline forms of Pitavastatin hemicalcium salt, referred to hereinafter as polymorphic Forms A, B, C, D, E and F, as well as the amorphous form. Furthermore, the present invention is directed to processes for the preparation of these crystalline forms and the amorphous form and pharmaceutical compositions comprising these crystalline forms or the amorphous forms.

30 Claims, 9 Drawing Sheets

(56) References Cited

OTHER PUBLICATIONS

English Language Translation of Aug. 21, 2010 Third Party Observation Submitted in JP 2006-501977 (including excerpt from WO 03/064932, which is a counterpart to JP-A-2005-520814).
Suzuki, Mikio, Development Work for HMG-CoA Reductase Inhibitor NK-104, (2001), (partial English translation attached).
Certificate for Library Material stored in the National Diet Library, Development Work for HMG-CoA Reductase Inhibitor NK-104, Published (2001) Volume Heisei-13, Chief Librarian of Kansai-kan of National Diet Library, Kazuyuki Yamaguchi (partial English translation attached).
Jan. 21, 2010 Submission of References in JP 2006-501997 (JP counterpart to present application) with English translation.
Mar. 3, 2010 Submission of References in JP 2006-501997 (JP counterpart to present application) with English translation.
Mar. 26, 2010 Submission of References in JP 2006-501997 (JP counterpart to present application) with English translation.
Jun. 29, 2010 Office Action in JP 2006-501997 (JP counterpart to present application) with English translation.
Aug. 23, 2010 Submission of References in JP 2006-501997 (JP counterpart to present application) with English translation.
Dec. 27, 2010 Submission of References in JP 2006-501997 (JP counterpart to present application) with English translation.
Jan. 21, 2010 Submission of References in JP 2006-520594 (JP counterpart to related U.S. Appl. No. 13/487,289) with English translation.
Mar. 3, 2010 Submission of References in JP 2006-520594 (JP counterpart to related U.S. Appl. No. 13/487,289) with English translation.
Mar. 26, 2010 Submission of References in JP 2006-520594 (JP counterpart to related U.S. Appl. No. 13/487,289) with English translation.
Apr. 12, 2011 Office Action in JP 2006-520594 (JP counterpart to related U.S. Appl. No. 13/487,289) with English translation.
Akiba et al., "Six-Month Repeated Oral Toxicity Study of NK-104 in Rats," The Journal of Toxicological Sciences, vol. 23, Supplement V, 713-720, 1998.
Aug. 26, 2004 International Search Report in EP 2004-707232 (EP counterpart to present application).
Mar. 14, 2006 Office Action in EP 2004-707232 (EP counterpart to present application).
Dec. 14, 2006 Third Party Submission in EP 2004-707232 (EP counterpart to present application).
Aug. 11, 2008 Third Party Submission in EP 2004-707232 (EP counterpart to present application).
Feb. 17, 2010 Office Action in EP 2004-707232 (EP counterpart to present application).
Sep. 29, 2010 Third Party Submission in EP-2004-707232 (EP counterpart to present application).
Jan. 25, 2011 Office Action in EP 2004-707232 (EP counterpart to present application).
Jul. 15, 2005 International Search Report in EP 2004-807807 (EP counterpart to related U.S. Appl. No. 13/487,289).
Sorbera et al., "NK-104: Hypolipidemic HMG-CoA Reductase Inhibitor," Drugs of the Future 1998, 23(8), pp. 847-859.
Nov. 14, 2005 International Preliminary Report on Patentability in EP 2004-807807 (EP counterpart to related U.S. Appl. No. 13/487,289).
Jan. 19, 2007 Office Action in EP 2004-807807 (EP counterpart to related U.S. Appl. No. 13/487,289).
Apr. 4, 2008 Office Action in EP 2004-807807 (EP counterpart to related U.S. Appl. No. 13/487,289).
Aug. 2, 2010 Office Action in EP 2004-807807 (EP counterpart to related U.S. Appl. No. 13/487,289).
Sep. 29, 2010 Third Party Submission in EP 2004-807807 (EP counterpart to related U.S. Appl. No. 13/487,289).
Feb. 8, 2011 Office Action in EP 2004-807807 (EP counterpart to related U.S. Appl. No. 13/487,289).
Apr. 11, 2011 Third Party Submission in EP 2004-807807 (EP counterpart to related U.S. Appl. No. 13/487,289).
Byrn et al., Solid State Chemistry of Drugs, 2d ed., SSCI, Inc., 1998, pp. 59-64.
The United States Pharmacopeia 2011, The National Formulary, USP 34 NF 29, vol. 1.
Brittain, Polymorphism in Pharmaceutical Solids, 2d ed., Informa Healthcare USA, 1999, 2009.
Berge et al., "Pharmaceutical Salts," Journal of Pharmaceutical Sciences, vol. 66, No. 1, Jan. 1977, pp. 1 to 18.
Takahashi et al., "Synthesis of an Artificial HMG-CoA Reductase Inhibitor NK-104 via a Hydrosilylation-Cross-Coupling Reaction," Bull. Chem. Soc. Jpn., 68, 2649-2656 (1995).
Miyachi et al., "A Novel Synthetic Method of HMG-CoA Reductase Inhibitor NK-104 Via a Hydroboration-Cross Coupling Sequence," Tetrahedron Letters, vol. 34, No. 51, pp. 8267-8270, 1993.
Bhattacharya, et al., "Thermoanalytical and Crystallographic Methods," Polymorphism in Pharmaceutical Solids, Brittain H. ed., 2d ed., Informa Healthcare USA, Inc., 2009, pp. 318-335.
Ivanisevic, et al., "Uses of X-Ray Powder Diffraction in the Pharmaceutical Industry," Pharm. Form. Qual., 2011, pp. 30-33.
Evaluation Reports for Approval for Prescription Drug: Pitavastatin Calcium, LIVALO tablet 1 mg, LIVALO tablet 2 mg, http://www.info.pmda.do.jp/, made public Sep. 10, 2003, with partial English translation.
Feb. 5, 2013 Office Action in JP 2011-260984 (JP counterpart to related U.S. Appl. No. 13/487,289), with partial English translation.
Ogata, How to Operate Chemical Experiment, vol. 1, 1963, pp. 154-155, 185-199 (cited in Feb. 5, 2013 Office Action in JP 2011-260984).
Dec. 10, 2012 Submission of References in JP 2006-501997 (JP counterpart to present application) with English translation.
Nov. 6, 2012 Submission of References in JP 2006-520594 (JP counterpart to related U.S. Appl. No. 13/487,289), with English translation.
"Medical Supplies Interview Form: HMG-CoA reductase inhibitor designated drugs LIVALO Tablet 1 mg and LIVALO Tablet 2 mg," Japanese Society of Hospital Pharmacists, Sep. 2003, with English translation.
Aug. 19, 2010 Submission of References in JP 2006-501997 (JP counterpart to present application) with partial English translation.
Mar. 8, 2011 Office Action in JP 2006-501997 (JP counterpart to present application) with English translation.
Apr. 26, 2011 Submission of References in JP 2006-501997 (JP counterpart to present application).
Sep. 30, 2010 Submission of References in JP 2006-520594 (JP counterpart to related U.S. Appl. No. 13/487,289), with partial English translation.
Introductory Chemistry Course 2, Physical Chemistry, pp. 321-341, Aug. 28, 1997 (cited in Sep. 30, 2011 Submission of References in JP 2006-520594).
Apr. 26, 2011 Submission of References in JP 2006-520594 (JP counterpart to related U.S. Appl. No. 13/487,289), with partial English translation.
Japanese Pharmacopoeia, Fourteenth Edition, pp. 49-51 Mar. 30, 2011 (cited in Apr. 26, 2011 Submission of References in JP 2006-520594).
Mar. 27, 2012 Office Action in JP 2006-520594 (JP counterpart to related U.S. Appl. No. 13/487,289), with English translation.

\* cited by examiner

CRYSTALLINE FORMS OF PITAVASTATIN CALCIUM

CROSS REFERENCES TO RELATED APPLICATIONS

This application is a continuation of U.S. patent application Ser. No. 13/664,498, filed Oct. 31, 2012, now pending; which is a continuation of U.S. patent application Ser. No. 13/280,431, filed Oct. 25, 2011, now abandoned; which is a continuation of U.S. patent application Ser. No. 12/331,086, filed on Dec. 9, 2008, now abandoned; which is a continuation of U.S. patent application Ser. No. 10/544,752, filed on Aug. 8, 2005, now abandoned; which was a 371 of International Patent Application No. PCT/EP2004/050066, filed on Feb. 2, 2004, and claims priority to European Patent Application No. 03405080.7, filed on Feb. 12, 2003, the disclosures of which are incorporated herein by reference in their entireties.

The present invention is directed to new crystalline forms and the amorphous form of Pitavastatin calcium, processes for the preparation thereof and pharmaceutical compositions comprising these forms.

The present invention relates to new crystalline forms and the amorphous form of Pitavastatin calcium. Pitavastatin is also known by the names NK-104, Itavastatin and Nisvastatin. Pitavastatin calcium is known by the chemical name: (3R,5S)-7-[2-cyclopropyl-4-(4-fluorophenyl)quinolin-3-yl]-3,5-dihydroxy-6(E)-heptenoic acid hemicalcium salt. Pitavastatin calcium has the following formula:

Pitavastatin calcium has recently been developed as a new chemically synthesized and powerful statin by Kowa Company Ltd, Japan. On the basis of reported data, the potency of Pitavastatin is dose-dependent and appears to be equivalent to that of Atorvastatin. This new statin is safe and well tolerated in the treatment of patients with hypercholesterolaemia. Significant interactions with a number of other commonly used drugs can be considered to be extremely low.

Processes for the preparation of Pitavastatin are described in EP-A-0304063 and EP-A-1099694 and in the publications by N. Miyachi et al. in Tetrahedron Letters (1993) vol. 34, pages 8267-8270 and by K. Takahashi et al. in Bull. Chem. Soc. Jpn. (1995) vol. 68, 2649-2656. These publications describe the synthesis of Pitavastatin in great detail but do not describe the hemicalcium salt of Pitavastatin. The publications by L. A. Sorbera et al. in Drugs of the Future (1998) vol. 23, pages 847-859 and by M. Suzuki et al. in Bioorganic & Medicinal Chemistry Letters (1999) vol. 9, pages 2977-2982 describe Pitavastatin calcium, however, a precise procedure for its preparation is not given. A full synthetic procedure for the preparation of Pitavastatin calcium is described in EP-A-0520406. In the process described in this patent Pitavastatin calcium is obtained by precipitation from an aqueous solution as a white crystalline material with a melting point of 190-192 C. It is known that pharmaceutical substances can exhibit polymorphism. Polymorphism is commonly defined as the ability of any substance to have two or more different crystal structures. Drug substances may also encapsulate solvent molecules when crystallized. These solvates or hydrates are referred to as pseudopolymorphs. It is also possible that the amorphous form is encountered. Different polymorphs, pseudopolymorphs or the amorphous form differ in their physical properties such as melting point, solubility etc. These can appreciably influence pharmaceutical properties such as dissolution rate and bioavailability. It is also economically desirable that the product is stable for extended periods of time without the need for specialized storage conditions. It is therefore important to evaluate polymorphism of drug substances. Furthermore, the discovery of new crystalline polymorphic forms of a drug enlarge the repertoire of materials that a formulation scientist has with which to design a pharmaceutical dosage form of a drug with a targeted release profile or other desired characteristics. We now have surprisingly found novel crystalline forms of Pitavastatin calcium, herein designated as form A, B, C, D, E and F, and the amorphous form of Pitavastatin calcium.

Accordingly, the present invention is directed to the polymorphic Forms A, B, C, D, E and F, and the amorphous form of Pitavastatin calcium salt (2:1).

One object of the invention is a crystalline polymorph of (3R,5S)-7-[2-cyclopropyl-4-(4-fluorophenyl) quinolin-3-yl]-3,5-dihydroxy-6(E)-heptenoic acid hemicalcium salt, herein designated as Form A, which exhibits a characteristic X-ray powder diffraction pattern with characteristic peaks expressed in d-values (Å) and in 2θ as given in Table 1 (vs=very strong intensity, s=strong intensity, m=medium intensity, w=weak intensity, vw=very weak intensity).

TABLE 1

| d-spacings and 2θ angles for Form A. | | |
|---|---|---|
| d-spacing [Å] | Angle [2θ] | Rel. Intensity |
| 17.6 | 5.0 | s |
| 13.0 | 6.8 | s |
| 9.7 | 9.1 | s |
| 8.8 | 10.0 | w |
| 8.4 | 10.5 | m |
| 8.1 | 11.0 | m |
| 6.7 | 13.3 | vw |
| 6.5 | 13.7 | s |
| 6.3 | 14.0 | w |
| 6.0 | 14.7 | w |
| 5.57 | 15.9 | vw |
| 5.25 | 16.9 | w |
| 5.17 | 17.1 | vw |
| 4.82 | 18.4 | m |
| 4.64 | 19.1 | w |
| 4.27 | 20.8 | vs |
| 4.20 | 21.1 | m |
| 4.10 | 21.6 | m |
| 3.87 | 22.9 | m |
| 3.74 | 23.7 | m |
| 3.67 | 24.2 | s |
| 3.53 | 25.2 | w |
| 3.29 | 27.1 | m |
| 3.02 | 29.6 | vw |
| 2.95 | 30.2 | w |
| 2.63 | 34.0 | w |

Another object of the invention is a crystalline polymorph of (3R,5S)-7-[2-cyclopropyl-4-(4-fluorophenyl)quinolin-3-yl]-3,5-dihydroxy-6(E)-heptenoic acid hemicalcium salt, herein designated as Form B, which exhibits a characteristic X-ray powder diffraction pattern with characteristic peaks expressed in d-values (Å) and in 2θ as given in Table 2.

TABLE 2 d-spacings and 2θ angles for Form B.

| d-spacing [Å] | Angle [2θ] | Rel. Intensity |
|---|---|---|
| 19.0 | 4.6 | w |
| 16.6 | 5.3 | vs |
| 14.2 | 6.2 | s |
| 11.5 | 7.7 | s |
| 9.6 | 9.2 | m |
| 9.2 | 9.6 | m |
| 8.5 | 10.3 | w |
| 7.8 | 11.3 | m |
| 7.6 | 11.7 | w |
| 7.0 | 12.6 | vw |
| 6.8 | 13.0 | w |
| 6.4 | 13.9 | m |
| 6.0 | 14.7 | vw |
| 5.94 | 14.9 | w |
| 5.66 | 15.6 | w |
| 5.43 | 16.3 | m |
| 5.22 | 17.0 | vw |
| 5.10 | 17.4 | vw |
| 4.92 | 18.0 | w |
| 4.74 | 18.7 | m |
| 4.59 | 19.3 | m |
| 4.43 | 20.0 | s |
| 4.33 | 20.5 | w |
| 4.26 | 20.8 | m |
| 4.19 | 21.2 | w, shoulder |
| 4.13 | 21.5 | m |
| 3.97 | 22.4 | m |
| 3.83 | 23.2 | s |
| 3.73 | 23.6 | m |
| 3.64 | 24.4 | vw |
| 3.53 | 25.2 | w, broad |
| 3.42 | 26.0 | w |
| 3.37 | 26.4 | vw |
| 3.30 | 27.0 | w |
| 3.19 | 27.9 | vw |
| 3.09 | 28.9 | w |

Another object of the invention is a crystalline polymorph of (3R,5S)-7-[2-cyclopropyl-4-(4-fluorophenyl)quinolin-3-yl]-3,5-dihydroxy-6(E)-heptenoic acid hemicalcium salt, herein designated as Form C, which exhibits a characteristic X-ray powder diffraction pattern with characteristic peaks expressed in d-values (Å) and in 2θ as given in Table 3.

TABLE 3 d-spacings and 2θ angles for Form C.

| d-spacing [Å] | Angle [2θ] | Rel. Intensity |
|---|---|---|
| 21.6 | 4.1 | m |
| 15.9 | 5.6 | s |
| 11.4 | 7.8 | m |
| 10.6 | 8.3 | m |
| 8.6 | 10.3 | m |
| 7.7 | 11.6 | w |
| 5.06 | 17.5 | w |
| 4.95 | 17.9 | w |
| 4.74 | 18.7 | m |
| 4.55 | 19.5 | s |
| 4.31 | 20.6 | m |
| 4.13 | 21.5 | vw |
| 4.06 | 21.9 | m |
| 3.84 | 23.1 | m |
| 3.71 | 24.0 | w |
| 3.58 | 24.8 | w |

Another object of the invention is a crystalline polymorph of (3R,5S)-7-[2-cyclopropyl-4-(4-fluorophenyl)quinolin-3-yl]-3,5-dihydroxy-6(E)-heptenoic acid hemicalcium salt, herein designated as Form D, which exhibits a characteristic X-ray powder diffraction pattern with characteristic peaks expressed in d-values (Å) and in 2θ as given in Table 4.

TABLE 4 d-spacings and 2θ angles for Form D.

| d-spacing [Å] | Angle [2θ] | Rel. Intensity |
|---|---|---|
| 17.5 | 5.0 | m |
| 13.5 | 6.5 | m |
| 13.0 | 6.8 | s |
| 10.1 | 8.7 | m |
| 8.8 | 10.0 | m |
| 8.6 | 10.2 | m |
| 8.2 | 10.8 | m |
| 6.8 | 13.1 | w |
| 6.55 | 13.5 | m |
| 6.20 | 14.3 | s |
| 5.78 | 15.3 | vw |
| 5.52 | 16.1 | m |
| 5.28 | 16.8 | w |
| 4.87 | 18.2 | w |
| 4.80 | 18.5 | m |
| 4.66 | 19.0 | w |
| 4.46 | 19.9 | m |
| 4.34 | 20.5 | m |
| 4.23 | 21.0 | vs |
| 4.09 | 21.7 | s |
| 3.99 | 22.3 | w |
| 3.80 | 23.4 | m |
| 3.70 | 24.0 | m |
| 3.47 | 25.6 | w |
| 3.40 | 26.2 | m |

Another object of the invention is a crystalline polymorph of (3R,5S)-7-[2-cyclopropyl-4-(4-fluorophenyl)quinolin-3-yl]-3,5-dihydroxy-6(E)-heptenoic acid hemicalcium salt, herein designated as Form E, which exhibits a characteristic X-ray powder diffraction pattern with characteristic peaks expressed in d-values (Å) and in 2θ as given in Table 5.

TABLE 5 d-spacings and 2θ angles for Form E.

| d-spacing [Å] | Angle [2θ] | Rel. Intensity |
|---|---|---|
| 20.0 | 4.4 | vw |
| 17.7 | 5.0 | s |
| 13.4 | 6.6 | s |
| 13.1 | 6.8 | s |
| 10.0 | 8.9 | s |
| 8.8 | 10.0 | m |
| 8.6 | 10.3 | s |
| 8.2 | 10.8 | m |
| 6.6 | 13.3 | s |
| 6.5 | 13.6 | m |
| 6.3 | 14.0 | s |
| 5.84 | 15.2 | vw |
| 5.56 | 15.9 | w |
| 5.39 | 16.4 | w |
| 5.24 | 16.9 | vw |
| 4.99 | 17.8 | vw |
| 4.84 | 18.3 | m |
| 4.69 | 18.9 | w |
| 4.39 | 20.2 | vs |
| 4.34 | 20.4 | m |
| 4.30 | 20.7 | m |
| 4.24 | 20.9 | m |
| 4.21 | 21.1 | vs |
| 4.12 | 21.6 | m |
| 4.08 | 21.7 | m |
| 3.99 | 22.3 | m |
| 3.77 | 23.5 | m |
| 3.73 | 23.8 | m |
| 3.69 | 24.1 | w |

TABLE 5-continued d-spacings and 2θ angles for Form E.

| d-spacing [Å] | Angle [2θ] | Rel. Intensity |
|---|---|---|
| 3.60 | 24.7 | vw |
| 3.50 | 25.4 | vw |
| 3.35 | 26.6 | m |
| 2.96 | 30.2 | w |
| 2.64 | 34.0 | vw |

Another object of the invention is a crystalline polymorph of (3R,5S)-7-[2-cyclopropyl-4-(4-fluorophenyl)quinolin-3-yl]-3,5-dihydroxy-6(E)-heptenoic acid hemicalcium salt, herein designated as Form F, which exhibits a characteristic X-ray powder diffraction pattern with characteristic peaks expressed in d-values (Å) and in 2θ as given in Table 6.

TABLE 6 d-spacing and 2θ angles for Form F.

| d-spacing [Å] | Angle [2θ] | Rel. Intensity |
|---|---|---|
| 17.2 | 5.1 | m |
| 15.8 | 5.6 | w |
| 12.6 | 7.0 | s |
| 10.0 | 8.8 | m |
| 9.2 | 9.6 | s |
| 8.7 | 10.2 | w |
| 8.1 | 10.9 | m |
| 7.8 | 11.3 | w |
| 7.4 | 11.9 | m |
| 7.1 | 12.5 | m |
| 6.8 | 13.0 | s |
| 6.5 | 13.7 | m |
| 6.2 | 14.4 | s |
| 8.04 | 14.7 | m |
| 5.79 | 15.3 | vw |
| 5.70 | 15.5 | w |
| 5.28 | 16.8 | m |
| 5.03 | 17.6 | w |
| 4.85 | 18.3 | m |
| 4.61 | 19.3 | m |
| 4.51 | 19.7 | m |
| 4.30 | 20.6 | m |
| 4.18 | 21.2 | vs |
| 4.08 | 21.8 | s |
| 3.90 | 22.8 | s |
| 3.84 | 23.1 | w |
| 3.74 | 23.8 | w, shoulder |
| 3.69 | 24.1 | s |
| 3.59 | 24.8 | s |
| 3.46 | 25.7 | m |
| 3.40 | 26.2 | vw |
| 3.35 | 26.6 | m |
| 3.31 | 26.9 | w |
| 3.14 | 28.4 | w |
| 3.02 | 29.5 | w |
| 3.00 | 29.8 | vw |
| 2.89 | 30.9 | m |

Small changes in the experimental details can cause small deviation in the d-values and 2θ of characteristic peaks in the X-ray powder diffraction patterns.

Figure 7A:
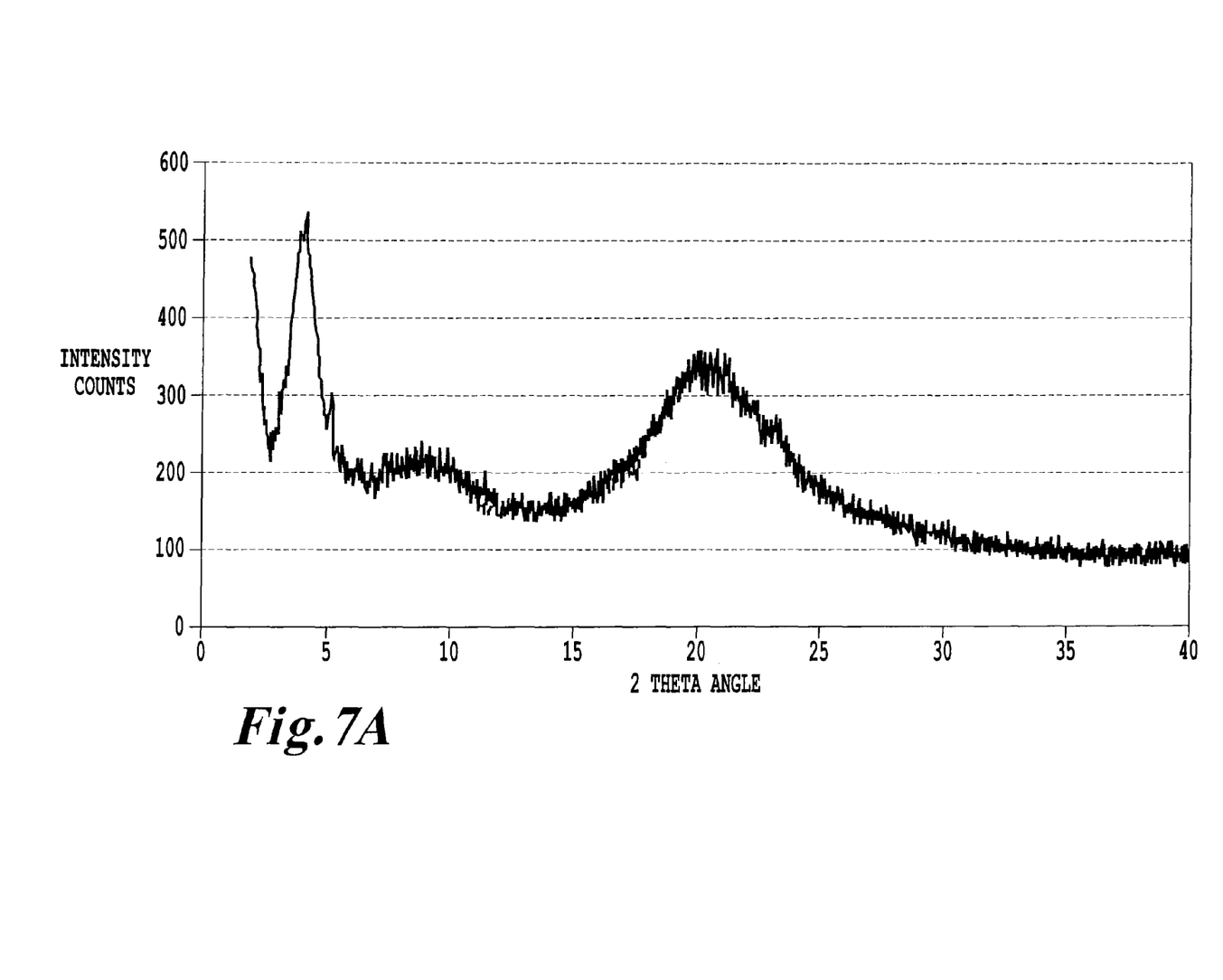
FIGS. 7A and 7B are two characteristic X-ray powder diffraction patterns for the amorphous form.
Figure 7B:
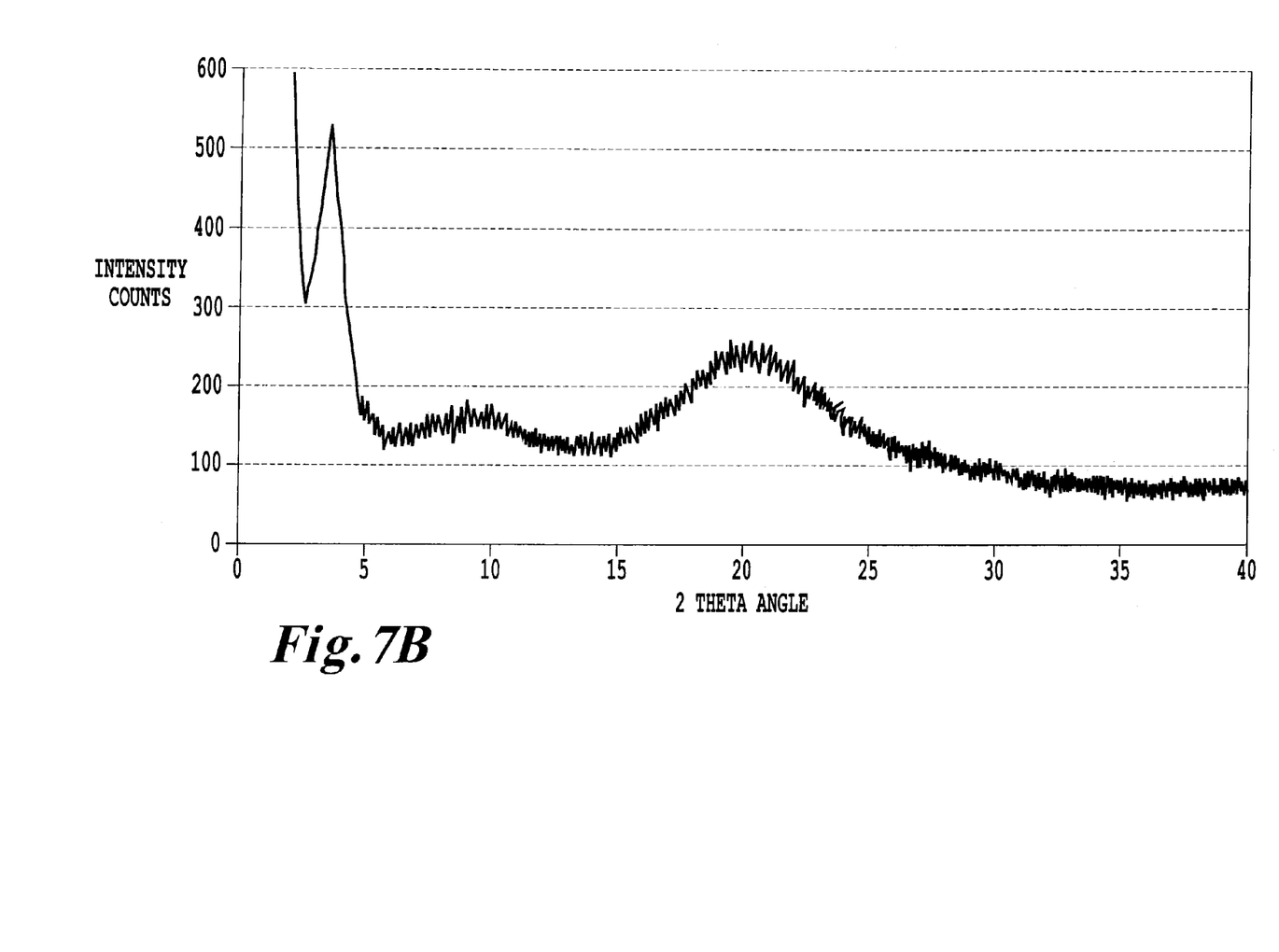

Another object of the invention is the amorphous form of (3R,5S)-7-[2-cyclopropyl-4-(4-fluorophenyl)quinolin-3-yl]-3,5-dihydroxy-6(E)-heptenoic acid hemicalcium salt which exhibits characteristic X-ray powder diffraction patterns as depicted in FIG. 7.

Powder X-ray diffraction is performed on a Philips 1710 powder X-ray diffractometer using Cu k (α1) radiation (1.54060 Å); 2θ angles are recorded with an experimental error of ±0.1-0.2°. A discussion of the theory of X-ray powder diffraction patterns can be found in "X-ray diffraction procedures" by H. P. Klug and L. E. Alexander, J. Wiley, New York (1974).

Furthermore, the present invention is directed to processes for the preparation of Form A, B, C, D, E and F, and the amorphous form of Pitavastatin calcium.

Form A can be generally prepared from Pitavastatin sodium upon reaction with $CaCl_2$ in an aqueous reaction medium. Alternatively, Form A of the invention may also be obtained in situ from the free acid ((3R,5S)-7-[2-cyclopropyl-4-(4-fluorophenyl)quinolin-3-yl]-3,5-dihydroxy-6(E)-heptenoic acid) or the corresponding lactone with $Ca(OH)_2$, advantageously also in an aqueous reaction medium. The aqueous reaction medium usually contains at least 80% b.w. of water; preferably it is water or water containing minor amounts of solvents and/or reactants from previous steps. Form A may contain up to 15% water, preferably about 3 to 12%, more preferably 9 to 11% of water.

Form B can be generally prepared by suspending form A in ethanol containing water as a co solvent. The amount of water is preferably about 1 to 50%.

Form C can be generally prepared by suspending form A in isopropanol containing water as a co solvent. The amount of water is preferably about 1 to 50%, especially 1 to 20% and more preferably about 5%. Form C can also be prepared from a mixture of isopropanol and a ketone solvent, containing water as a co solvent. Preferably, the ketone solvent is acetone, and the amount of ketone solvent are about 1 to 30%, more preferably about 10%. The amount of water is preferably about 1 to 20%, more preferably about 5%.

Form D can be generally prepared by suspending form A in absolute ethanol.

Form E can be generally prepared by suspending form A in 1,4-dioxane containing water as a co solvent. The amount of water is preferably about 1 to 50%.

Form F can be generally prepared by suspending form A in methanol containing water as a co solvent. The amount of water is preferably about 1 to 50%.

In the above mentioned processes small amounts of seeding crystals of the desired crystalline form may be added to the reaction mixture. Preferably small amounts are about 1 to 20 weight %, more preferably about 5 weight %. Seeding crystals may be added before or, where appropriate, after the step initiating the crystallization (e.g. cooling, addition of non-solvent etc. as described above). Addition before initiating the crystallization is of specific technical interest.

The amorphous form can be generally prepared by addition of a non-solvent to a concentrated solution of Pitavastatin calcium in an organic solvent. As non-solvent may be taken for example heptane or methyl tert-butyl ether, whereas examples for the organic solvent are 1,4-dioxane, tetrahydrofuran and ethyl methyl ketone. It is preferable that the non-solvent and solvent are miscible. The amorphous form can also be prepared by lyophilization of an aqueous solution of Pitavastatin calcium.

Preparations of polymorphic forms A, B, C, D, E, F as well as the amorphous form are usually done in substantially pure reaction systems, essentially consisting of the educt specified, preferably in substantially crystalline form, and solvents and/or non-solvents as given above.

Another object of the present invention are processes for the preparation of crystalline forms of Pitavastatin calcium essentially free of residual organic solvent.

Particularly, the present invention is related to processes for the preparation of crystalline forms of Pitavastatin calcium essentially free of residual organic solvent by exposing the crystalline form of Pitavastatin calcium to an atmosphere with a defined relative air humidity. More particularly, the present invention is directed to a process for the preparation of any crystalline form or amorphous form of Pitavastatin calcium which is essentially free of residual organic solvent. These can, for example, be prepared by exposing the crystalline form or amorphous form to an atmosphere with a relative air humidity of 5 to 100%. Preferably, these are prepared by exposure to an inert gas stream with a defined relative air humidity to exchange residual organic solvent with water. In general, a relative air humidity of 5 to 100%, especially 40 to 80%, is used.

Another object of the present invention are pharmaceutical compositions comprising an effective amount of crystalline polymorphic Form A, B, C, D, E or F or the amorphous form of Pitavastatin calcium, and a pharmaceutical acceptable carrier.

These polymorphic forms may be used as single component or as mixtures with other crystalline forms or the amorphous form.

As to the novel polymorphic forms and amorphous form of Pitavastatin calcium it is preferred that these contain 25-100% by weight, especially 50-100% by weight, of at least one of the novel forms, based on the total amount of Pitavastatin calcium. Preferably, such an amount of the novel polymorphic forms or amorphous form of Pitavastatin calcium is 75-100% by weight, especially 90-100% by weight. Highly preferred is an amount of 95-100% by weight.

The compositions of the invention include powders, granulates, aggregates and other solid compositions comprising at least one of the novel forms. In addition, the compositions that are contemplated by the present invention may further include diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl, cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin.

Further excipients that are within the contemplation of the present invention include binders, such as acacia gum, pregelatinized starch, sodium alginate, glucose and other binders used in wet and dry granulation and direct compression tableting processes. Excipients that also may be present in the solid compositions further include disintegrants like sodium starch glycolat, crospovidone, low-substituted hydroxypropyl cellulose and others. In addition, excipients may include tableting lubricants like magnesium and calcium stearate and sodium stearyl fumarate; flavorings; sweeteners; preservatives; pharmaceutically acceptable dyes and glidants such as silicon dioxide.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the art of pharmacy.

Dosage forms include solid dosage forms, like tablets, powders, capsules, suppositories, sachets, troches and lozenges as well as liquid suspensions and elixirs. While the description is not intended to be limiting, the invention is also not intended to pertain to true solutions of Pitavastatin calcium whereupon the properties that distinguish the solid forms of Pitavastatin calcium are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Preferred unit dosages of the pharmaceutical compositions of this invention typically contain from 0.5 to 100 mg of the novel Pitavastatin calcium forms or mixtures thereof with each other or other forms of Pitavastatin calcium. More usually, the combined weight of the Pitavastatin calcium forms of a unit dosage are from 2.5 mg to 80 mg, for example 5, 10, 20 or 40 mg.

The following Examples illustrate the invention in more detail. Temperatures are given in degrees Celsius.

EXAMPLE 1

Figure 1:
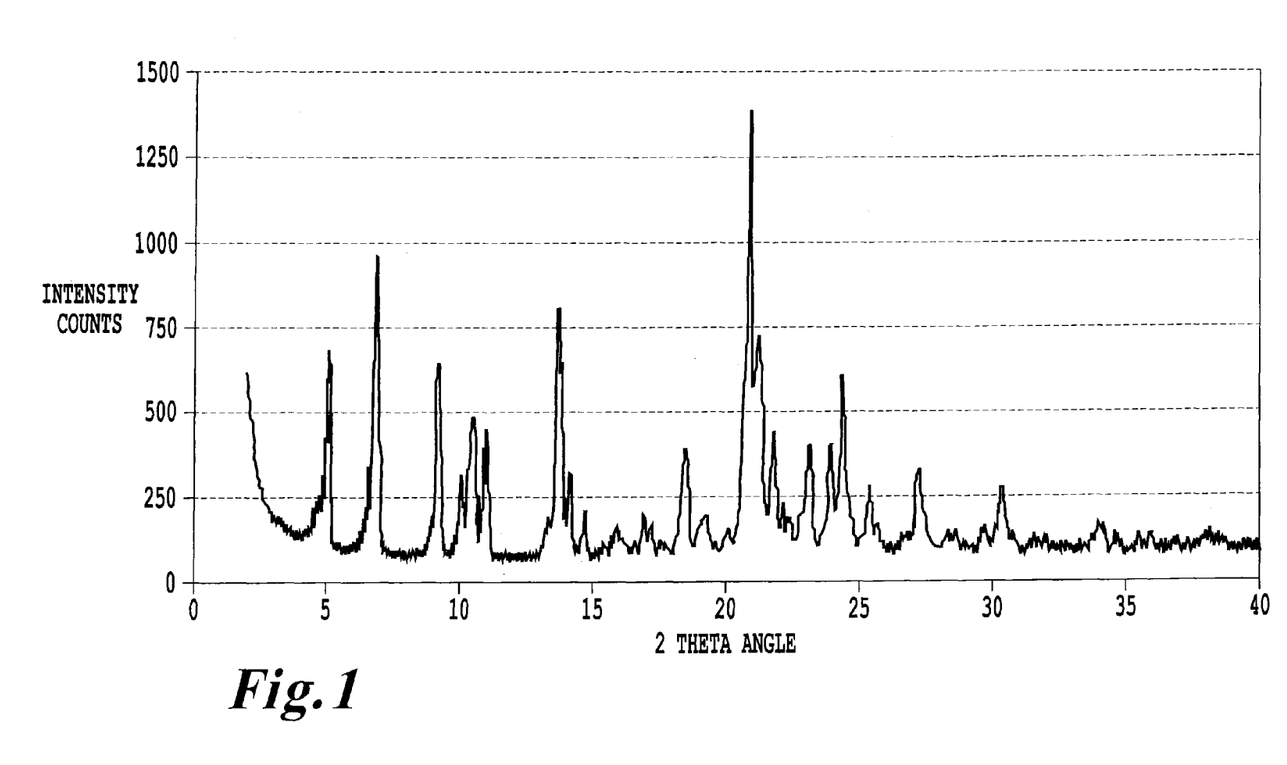
FIG. 1 is a characteristic X-ray powder diffraction pattern for Form A.

Preparation of Form A 4.15 gr of (3R,5S)-7-[2-cyclopropyl-4-(4-fluorophenyl) quinolin-3-yl]-3,5-dihydroxy-6(E)-heptenoic acid tert-butyl ester (Pitavastatin tert-butyl ester) was suspended in 52 ml of a mixture of methyl tert-butyl ether and methanol (10:3). To this mixture were added 2.17 ml of a 4M aqueous solution of NaOH, and the resulting yellowish solution was stirred for 2.5 hours at 50° C. The reaction mixture was cooled to room temperature followed by the addition of 50 ml water and stirring for an additional hour. The aqueous phase was separated and once extracted with 20 ml of methyl tert-butyl ether. To this aqueous solution were added a solution of 0.58 gr $CaCl_2$ in 80 ml of water over a period of 1 hour. The resulting suspension was stirred for about 16 hours at room temperature. The suspension was filtered and the obtained solid was dried at 40° C. and 50 mbar for about 16 hours. The obtained product is crystal Form A which is characterized by an X-ray powder diffraction pattern as shown in FIG. 1. Further characterization of the obtained Form A by thermogravimetry coupled with FT-IR spectroscopy revealed a water content of about 10%. Differential scanning calorimetry revealed a melting point of 95° C.

EXAMPLE 2

Figure 2:
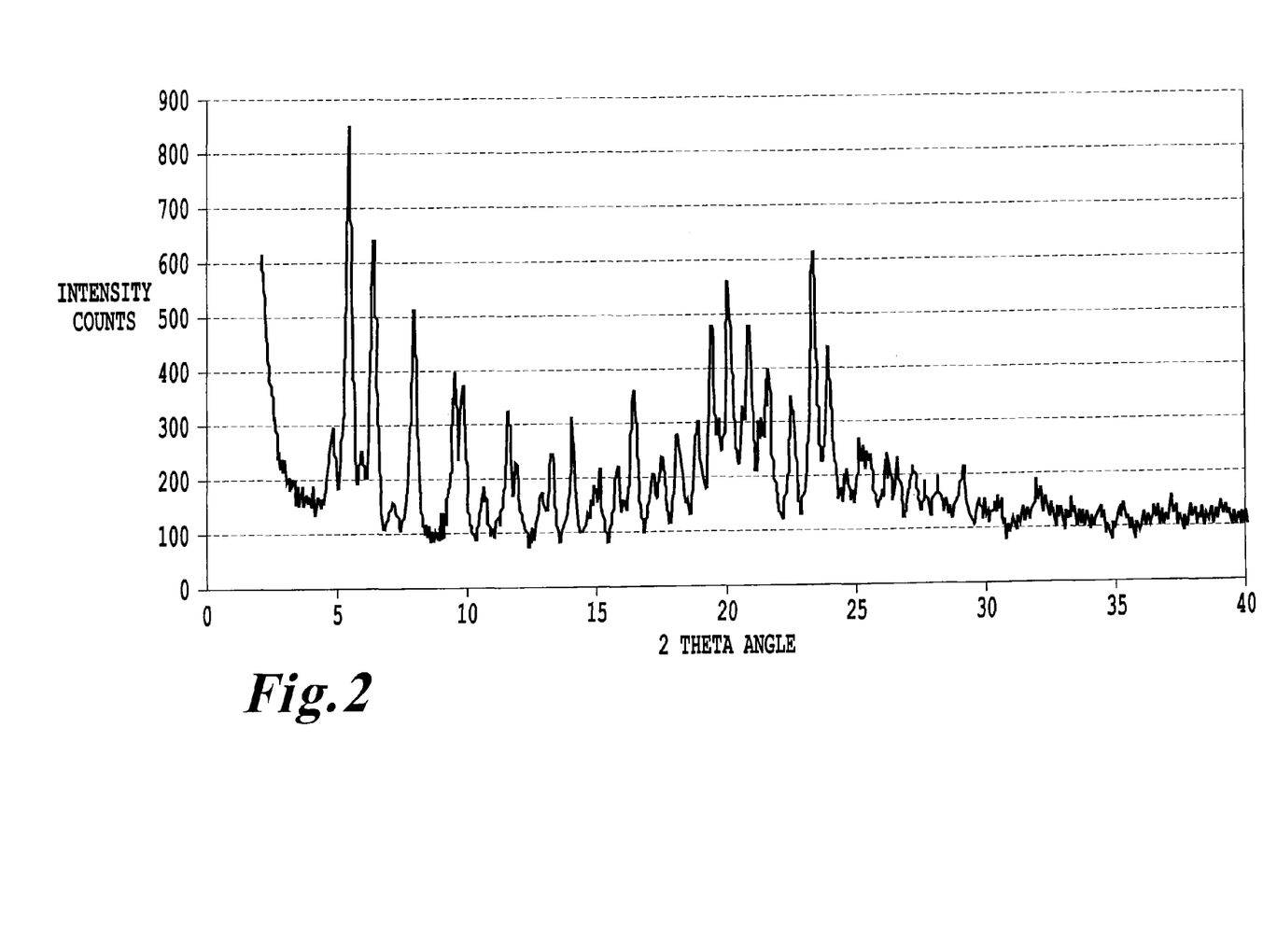
FIG. 2 is a characteristic X-ray powder diffraction pattern for Form B.

Preparation of Form B 100 mg Pitavastatin calcium Form A was suspended in 2 ml water and stirred at room temperature for 30 min, followed by the addition of 2 ml of ethanol and additional stirring for 18 hours. The suspension was filtered and dried in air, yielding 36 mg of Form B. The obtained crystal Form B is characterized by an X-ray powder diffraction pattern as shown in FIG.

2. Further characterization of the obtained Form B by thermogravimetry coupled with FT-IR spectroscopy revealed a water content of about 10%.

EXAMPLE 3

Figure 3A:
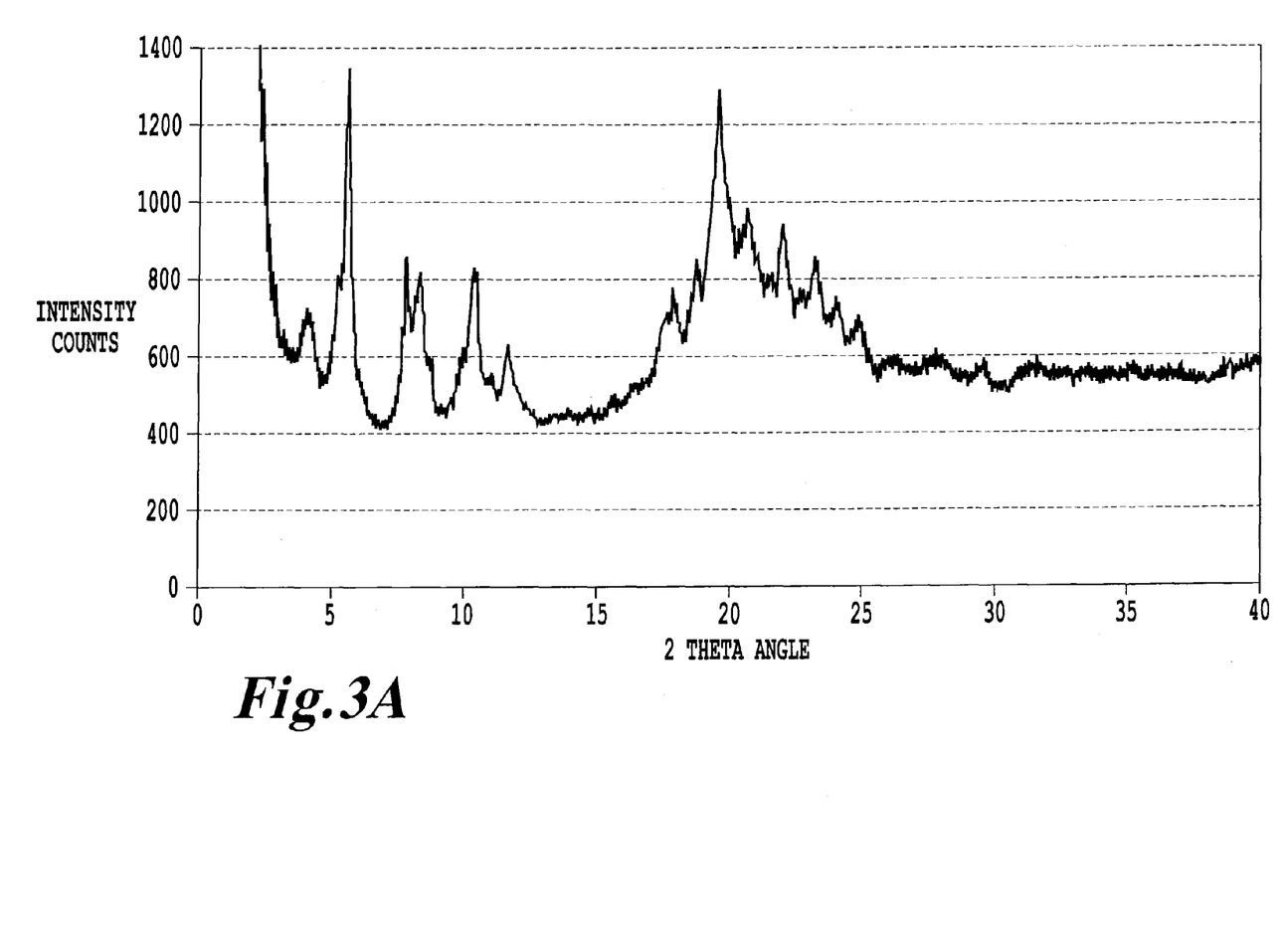
FIGS. 3A and 3B are two characteristic X-ray powder diffraction patterns for Form C.

Preparation of Form C 62 mg Pitavastatin calcium Form A was suspended in 2 ml isopropanol containing 5% water. This suspension was heated to 60° C., which led to almost complete dissolution of Form A, and again cooled to room temperature. At this temperature the suspension was stirred for 66 hours. The resulting suspension was filtered, once washed with some isopropanol containing 5% water, and dried in air. The obtained crystal Form C is characterized by an X-ray powder diffraction pattern as shown in FIG. 3. Further characterization of the obtained Form C by thermogravimetry coupled with FT-IR spectroscopy revealed that the sample contains about 6.3% isopropanol and a small amount of water.

EXAMPLE 4

Figure 3B:
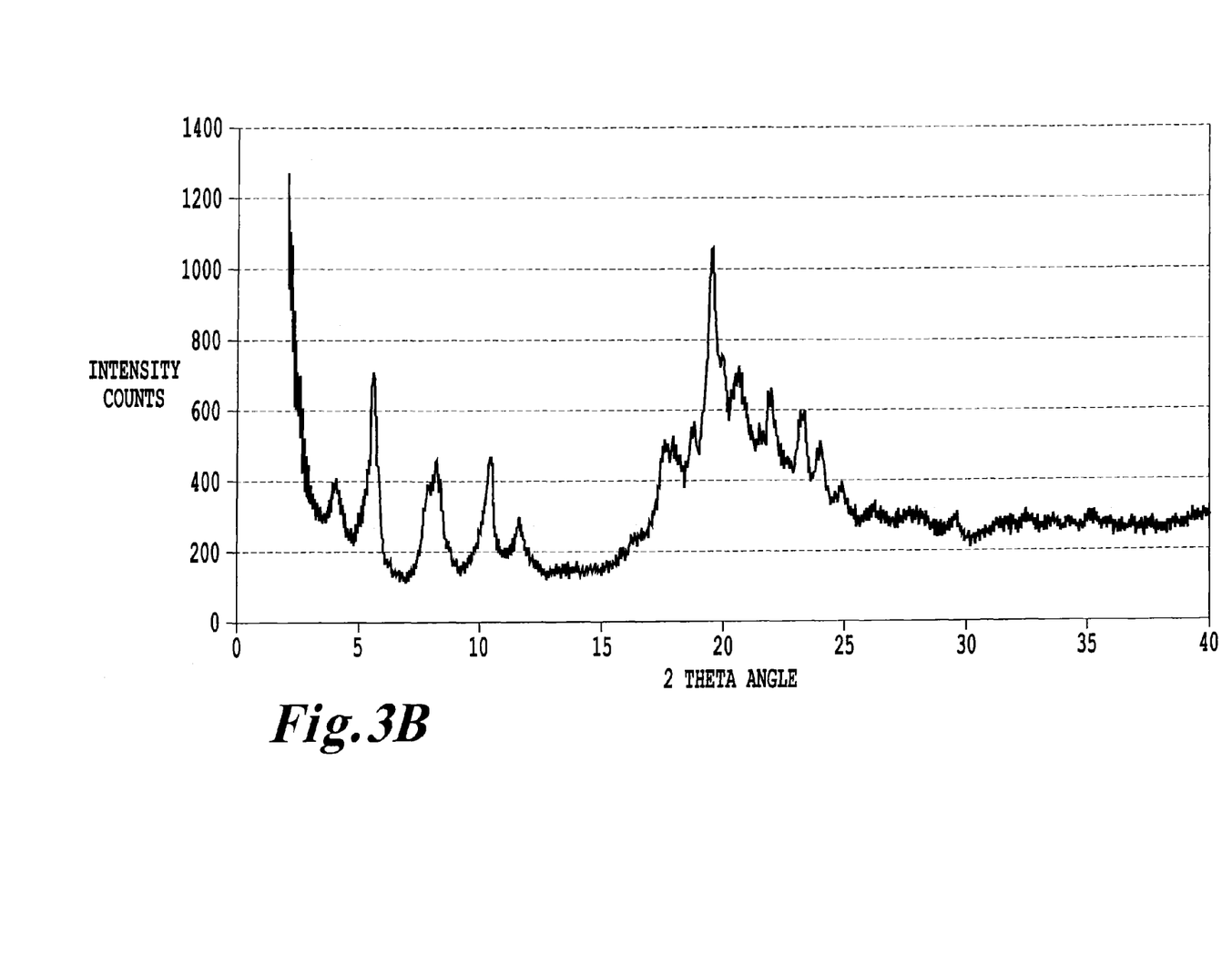

Preparation of Form C 65 mg Pitavastatin calcium Form A was suspended in a mixture of 0.9 ml isopropanol, 0.1 ml acetone and 40 µl water. Stirring this suspension for about 1 hour led to nearly complete dissolution. Seeding with 4 mg of Form C (from example 3) and stirring for 2 hours led to the formation of a concentrated suspension. This suspension was diluted with the same amount of solvent mixture as above and stirred for an additional 40 hours. The suspension was filtered and the obtained solid was dried at 40° C. for about 10 min. Analysis by X-ray powder diffraction indicates the product to be crystal Form C as shown in FIG. 3.

EXAMPLE 5

Figure 4:
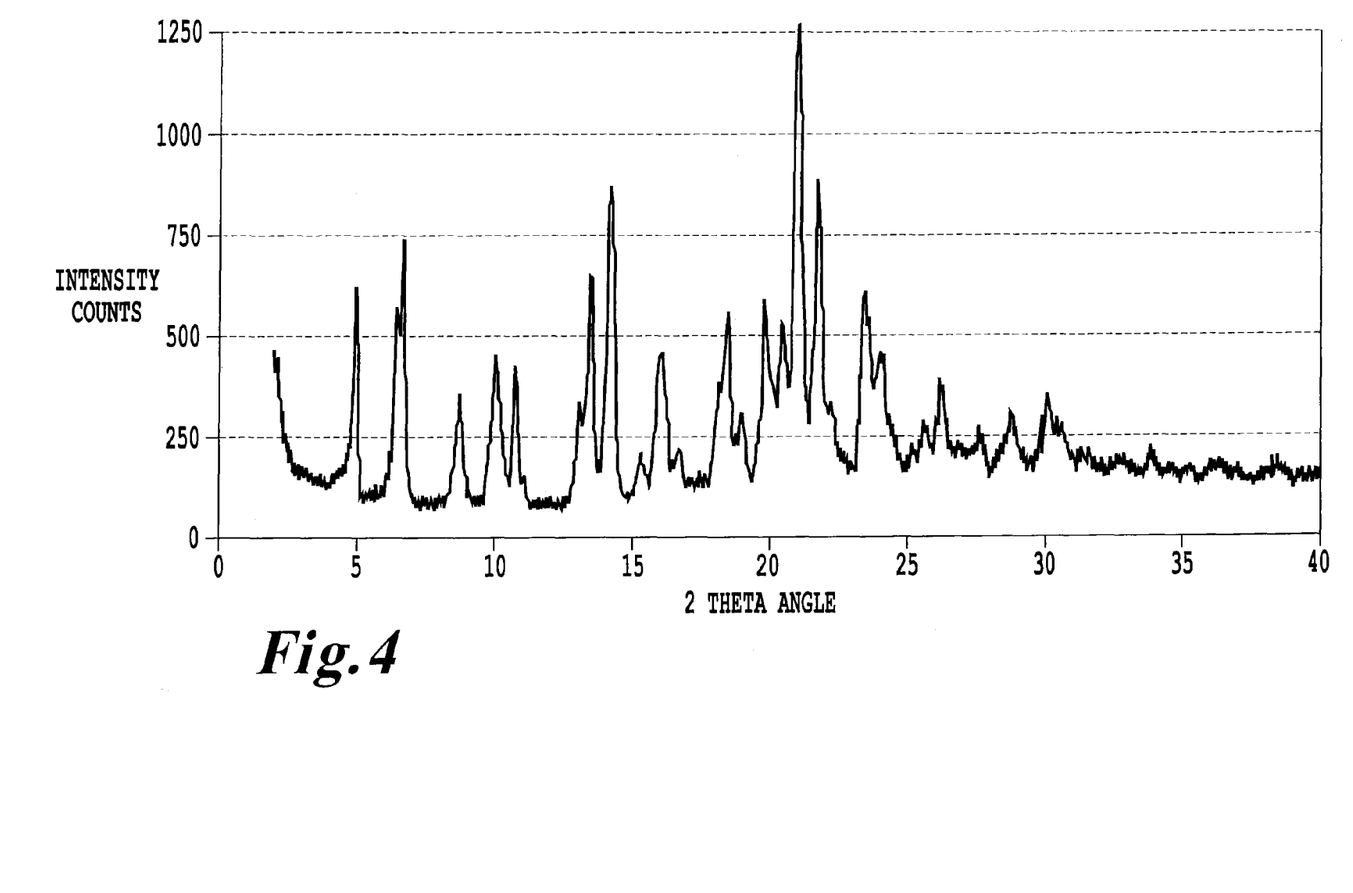
FIG. 4 is a characteristic X-ray powder diffraction pattern for Form D.

Preparation of Form D 60 mg of Pitavastatin calcium Form A was suspended in 1 ml absolute ethanol and stirred at room temperature for 20 hours. The resulting suspension was filtered and dried in air. The obtained crystal Form D is characterized by an X-ray powder diffraction pattern as shown in FIG. 4.

EXAMPLE 6

Figure 5:
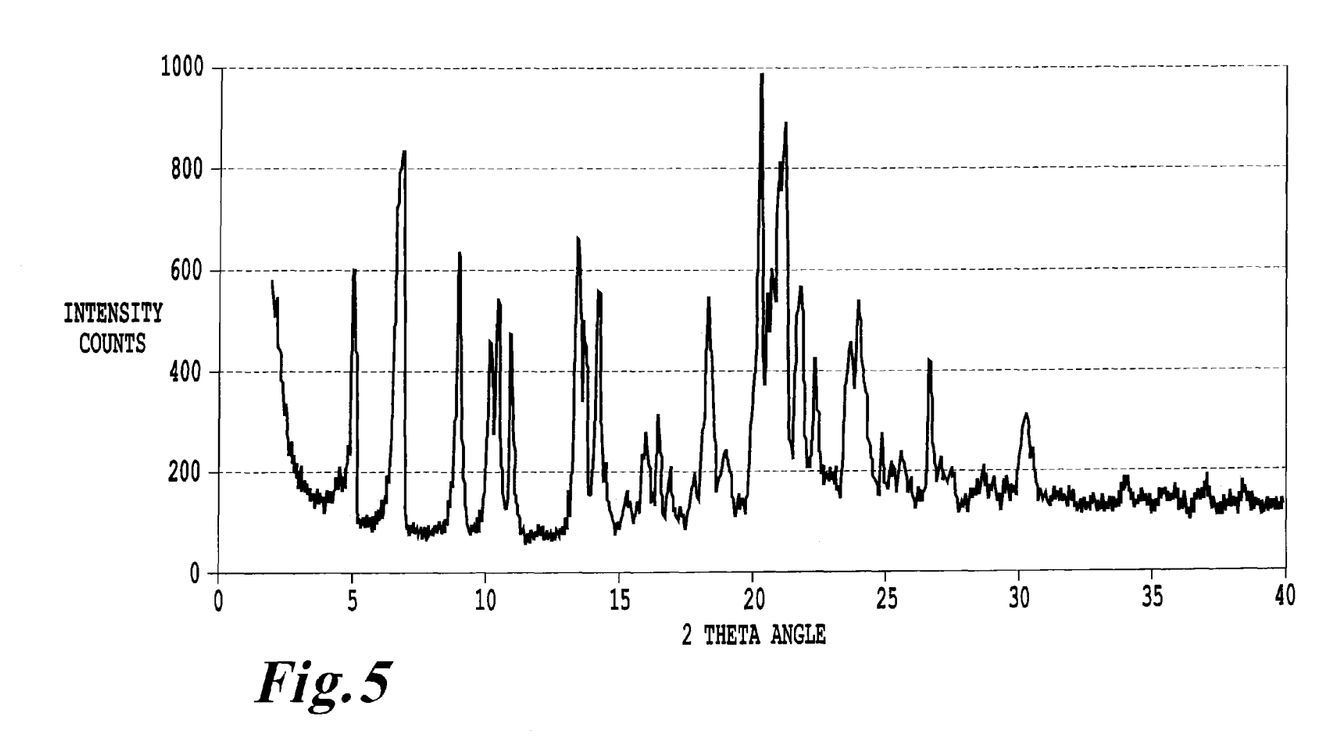
FIG. 5 is a characteristic X-ray powder diffraction pattern for Form E.

Preparation of Form E 60 mg of Pitavastatin calcium Form A was suspended in a mixture of 1,4-dioxane and water (1:1), and stirred for 18 hours at room temperature. The resulting suspension was filtered and dried in air. The obtained crystal Form E is characterized by an X-ray powder diffraction pattern as shown in FIG. 5.

EXAMPLE 7

Figure 6:
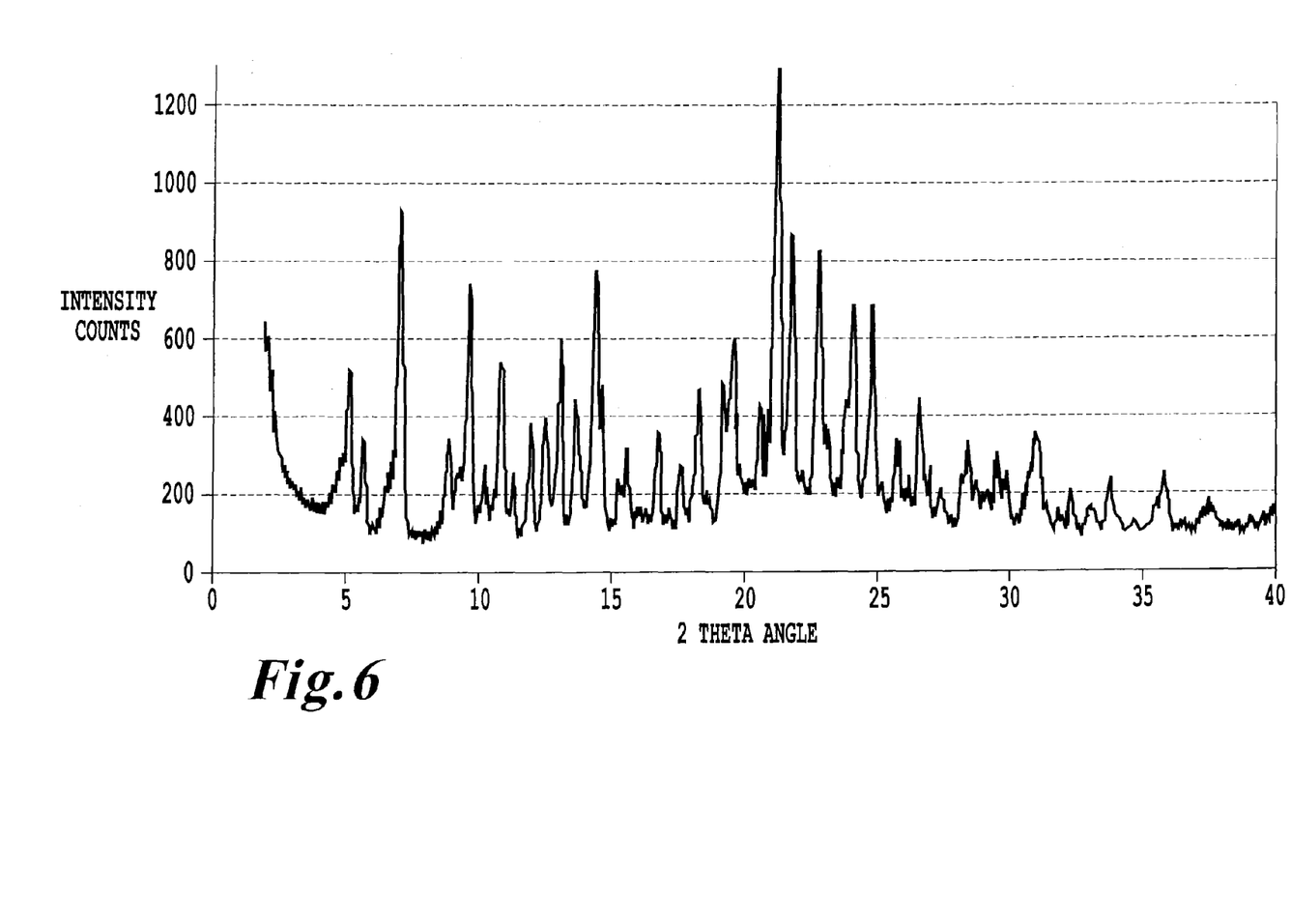
FIG. 6 is a characteristic X-ray powder diffraction pattern for Form F.

Preparation of Form F 60 mg of Pitavastatin calcium Form A was suspended in 3 ml methanol containing 20% water, and stirred at 40° C. for 1 hour. The resulting suspension was slowly cooled to room temperature and stirring was continued for 4 hours. The suspension was heated again to 40° C., stirred for 30 min, slowly cooled to room temperature and stirred for an additionally 15 hours. The suspension was filtered and the obtained white solid dried in air. The obtained crystal Form F is characterized by an X-ray powder diffraction pattern as shown in FIG. 6.

EXAMPLE 8

Preparation of the Amorphous Form 62 mg of Pitavastatin calcium Form A was dissolved in 0.3 ml 1,4-dioxane. To this stirred solution was slowly added 2.3 ml n-heptane at room temperature, and stirred for an additional 16 hours. The resulting suspension was filtered and dried in air. The obtained solid was amorphous as is shown by the X-ray diffraction pattern given in FIG. 7 (top).

EXAMPLE 9

Preparation of the Amorphous Form 60 mg of Pitavastatin calcium Form A was dissolved in 1.5 ml ethyl methyl ketone. To this solution was added in steps of 1 ml each 30 sec a total of 21 ml methyl tert-butyl ether. The resulting suspension was stirred at room temperature for about 16 hours. The suspension was filtered and the obtained solid was dried in air. An X-ray diffraction study on the product showed it to be amorphous, see FIG. 7 (bottom). Further characterization of the obtained product by thermogravimetry coupled with FT-IR spectroscopy revealed that the sample contained about 5.5% methyl tert-butyl ether. Differential scanning calorimetry showed the sample to have a glass transition temperature of about 68° C.

The invention claimed is:

1. A process for preparing a crystalline polymorph A of (3R,5S)-7-[2-cyclopropyl-4-(4-fluorophenyl)quinolin-3-yl]-3,5-dihydroxy-6(E)-heptenoic acid hemicalcium salt, which exhibits a characteristic X-ray powder diffraction pattern with characteristic peaks expressed in 2θ at 5.0 (s), 6.8 (s), 9.1 (s), 10.0 (w), 10.5 (m), 11.0 (m), 13.3 (vw), 13.7 (s), 14.0 (w), 14.7 (w), 15.9 (vw), 16.9 (w), 17.1 (vw), 18.4 (m), 19.1 (w), 20.8 (vs), 21.1 (m), 21.6 (m), 22.9 (m), 23.7 (m), 24.2 (s), 25.2 (w), 27.1 (m), 29.6 (vw), 30.2 (w), and 34.0 (w), wherein (vs) stands for very strong intensity, (s) stands for strong intensity, (m) stands for medium intensity, (w) stands for weak intensity, and (vw) stands for very weak intensity, the process comprising:

reacting (3R,5S)-7-[2-cyclopropyl-4-(4-fluorophenyl)quinolin-3-yl]-3,5-dihydroxy-6(E)-heptenoic acid sodium salt with $CaCl_2$ in an aqueous reaction medium or reacting the free acid (3R,5S)-7-[2-cyclopropyl-4-(4- fluorophenyl)quinolin-3-yl]-3,5-dihydroxy-6(E)-heptenoic acid or the corresponding lactone (4R,6S)-6-{(E)-2-[2-cyclopropyl-4-(4-fluorophenyl)quinolin-3-yl]-vinyl}-4-hydroxy-tetrahydropyran-2-one with Ca(OH)$_2$;

isolating the crystalline polymorph A; and exposing the isolated crystalline polymorph A to an atmosphere with a relative air humidity of 5 to 100%.

2. The process of claim 1, wherein exposing the isolated crystalline polymorph A to the atmosphere with the relative air humidity of 5 to 100%, comprises exposing the isolated crystalline polymorph A to an inert gas stream with a relative air humidity of 5 to 100%.

3. The process of claim 1, wherein the atmosphere has a relative air humidity of 40 to 80%.

4. A process for preparing a crystalline polymorph B of (3R,5S)-7-[2-cyclopropyl-4-(4-fluorophenyl)quinolin-3-yl]-3,5-dihydroxy-6(E)-heptenoic acid hemicalcium salt, which exhibits a characteristic X-ray powder diffraction pattern with characteristic peaks expressed in 2θ at 4.6 (w), 5.3 (vs), 6.2 (s), 7.7 (s), 9.2 (m), 9.6 (m), 10.3 (w), 11.3 (m), 11.7 (w), 12.6 (vw), 13.0 (w), 13.9 (m), 14.7 (vw), 14.9 (w), 15.6 (w), 16.3 (m), 17.0 (vw), 17.4 (vw), 18.0 (w), 18.7 (m), 19.3 (m), 20.0 (s), 20.5 (w), 20.8 (m), 21.2 (w, shoulder), 21.5 (m), 22.4 (m), 23.2 (s), 23.8 (m), 24.4 (vw), 25.2 (w, broad), 26.0 (w), 26.4 (vw), 27.0 (w), 27.9 (vw), and 28.9 (w), wherein (vs) stands for very strong intensity, (s) stands for strong intensity, (m) stands for medium intensity, (w) stands for weak intensity, and (vw) stands for very weak intensity, the process comprising:

suspending a crystalline polymorph A of (3R,5S)-7-[2-cyclopropyl-4-(4-fluorophenyl)quinolin-3-yl]-3,5-dihydroxy-6(E)-heptenoic acid hemicalcium salt in ethanol containing water as a cosolvent;

isolating the crystalline polymorph B; and exposing the isolated crystalline polymorph B to an atmosphere with a relative air humidity of 5 to 100%;

wherein the crystalline polymorph A exhibits a characteristic X-ray powder diffraction pattern with characteristic peaks expressed in 2θ at 5.0 (s), 6.8 (s), 9.1 (s), 10.0 (w), 10.5 (m), 11.0 (m), 13.3 (vw), 13.7 (s), 14.0 (w), 14.7 (w), 15.9 (vw), 16.9 (w), 17.1 (vw), 18.4 (m), 19.1 (w), 20.8 (vs), 21.1 (m), 21.6 (m), 22.9 (m), 23.7 (m), 24.2 (s), 25.2 (w), 27.1 (m), 29.6 (vw), 30.2 (w), and 34.0 (w), wherein (vs) stands for very strong intensity, (s) stands for strong intensity, (m) stands for medium intensity, (w) stands for weak intensity, and (vw) stands for very weak intensity.

5. The process of claim 4, wherein exposing the isolated crystalline polymorph B to the atmosphere with the relative air humidity of 5 to 100%, comprises exposing the isolated crystalline polymorph B to an inert gas stream with a relative air humidity of 5 to 100%.

6. The process of claim 4, wherein the atmosphere has a relative air humidity of 40 to 80%.

7. A process for preparing a crystalline polymorph C of (3R,5S)-7-[2-cyclopropyl-4-(4-fluorophenyl)quinolin-3-yl]-3,5-dihydroxy-6(E)-heptenoic acid hemicalcium salt, which exhibits a characteristic X-ray powder diffraction pattern with characteristic peaks expressed in 2θ at 4.1 (m), 5.6 (s), 7.8 (m), 8.3 (m), 10.3 (m), 11.6 (w), 17.5 (w), 17.9 (w), 18.7 (m), 19.5 (s), 20.6 (m), 21.5 (vw), 21.9 (m), 23.1 (m), 24.0 (w), and 24.8 (w), wherein (vs) stands for very strong intensity, (s) stands for strong intensity, (m) stands for medium intensity, (w) stands for weak intensity, and (vw) stands for very weak intensity, the process comprising:

suspending a crystalline polymorph A of (3R,5S)-7-[2-cyclopropyl-4-(4-fluorophenyl)quinolin-3-yl]-3,5-dihydroxy-6(E)-heptenoic acid hemicalcium salt in isopropanol containing water as a cosolvent;

isolating the crystalline polymorph C; and exposing the isolated crystalline polymorph C to an atmosphere with a relative air humidity of 5 to 100%;

wherein the crystalline polymorph A exhibits a characteristic X-ray powder diffraction pattern with characteristic peaks expressed in 2θ at 5.0 (s), 6.8 (s), 9.1 (s), 10.0 (w), 10.5 (m), 11.0 (m), 13.3 (vw), 13.7 (s), 14.0 (w), 14.7 (w), 15.9 (vw), 16.9 (w), 17.1 (vw), 18.4 (m), 19.1 (w), 20.8 (vs), 21.1 (m), 21.6 (m), 22.9 (m), 23.7 (m), 24.2 (s), 25.2 (w), 27.1 (m), 29.6 (vw), 30.2 (w), and 34.0 (w), wherein (vs) stands for very strong intensity, (s) stands for strong intensity, (m) stands for medium intensity, (w) stands for weak intensity, and (vw) stands for very weak intensity.

8. The process of claim 7, wherein exposing the isolated crystalline polymorph C to the atmosphere with the relative air humidity of 5 to 100%, comprises exposing the isolated crystalline polymorph C to an inert gas stream with a relative air humidity of 5 to 100%.

9. The process of claim 7, wherein the atmosphere has a relative air humidity of 40 to 80%.

10. A process for preparing a crystalline polymorph C of (3R,5S)-7-[2-cyclopropyl-4-(4-fluorophenyl)quinolin-3-yl]-3,5-dihydroxy-6(E)-heptenoic acid hemicalcium salt, which exhibits a characteristic X-ray powder diffraction pattern with characteristic peaks expressed in 2θ at 4.1 (m), 5.6 (s), 7.8 (m), 8.3 (m), 10.3 (m), 11.6 (w), 17.5 (w), 17.9 (w), 18.7 (m), 19.5 (s), 20.6 (m), 21.5 (vw), 21.9 (m), 23.1 (m), 24.0 (w), and 24.8 (w), wherein (vs) stands for very strong intensity, (s) stands for strong intensity, (m) stands for medium intensity, (w) stands for weak intensity, and (vw) stands for very weak intensity, the process comprising:

suspending a crystalline polymorph A of (3R,5S)-7-[2-cyclopropyl-4-(4-fluorophenyl)quinolin-3-yl]-3,5-dihydroxy-6(E)-heptenoic acid hemicalcium salt in a mixture of isopropanol and a ketone solvent, containing water as a cosolvent;

isolating the crystalline polymorph C; and exposing the isolated crystalline polymorph C to an atmosphere with a relative air humidity of 5 to 100%;

wherein the crystalline polymorph A exhibits a characteristic X-ray powder diffraction pattern with characteristic peaks expressed in 2θ at 5.0 (s), 6.8 (s), 9.1 (s), 10.0 (w), 10.5 (m), 11.0 (m), 13.3 (vw), 13.7 (s), 14.0 (w), 14.7 (w), 15.9 (vw), 16.9 (w), 17.1 (vw), 18.4 (m), 19.1 (w), 20.8 (vs), 21.1 (m), 21.6 (m), 22.9 (m), 23.7 (m), 24.2 (s), 25.2 (w), 27.1 (m), 29.6 (vw), 30.2 (w), and 34.0 (w), wherein (vs) stands for very strong intensity, (s) stands for strong intensity, (m) stands for medium intensity, (w) stands for weak intensity, and (vw) stands for very weak intensity.

11. The process of claim 10, wherein exposing the isolated crystalline polymorph C to the atmosphere with the relative air humidity of 5 to 100%, comprises exposing the isolated crystalline polymorph C to an inert gas stream with a relative air humidity of 5 to 100%.

12. The process of claim 10, wherein the atmosphere has a relative air humidity of 40 to 80%.

13. A process for preparing a crystalline polymorph D of (3R,5S)-7-[2-cyclopropyl-4-(4-fluorophenyl)quinolin-3-yl]-3,5-dihydroxy-6(E)-heptenoic acid hemicalcium salt, which exhibits a characteristic X-ray powder diffraction pattern with characteristic peaks expressed in 2θ at 5.0 (m), 6.5 (m), 6.8 (s), 8.7 (m), 10.0 (m), 10.2 (m), 10.8 (m), 13.1 (w), 13.5 (m), 14.3 (s), 15.3 (vw), 16.1 (m), 16.8 (w), 18.2 (w), 18.5 (m), 19.0 (w), 19.9 (m), 20.5 (m), 21.0 (vs), 21.7 (s), 22.3 (w), 23.4 (m), 24.0 (m), 25.6 (w), and 26.2 (m), wherein (vs) stands for very strong intensity, (s) stands for strong intensity, (m) stands for medium intensity, (w) stands for weak intensity, and (vw) stands for very weak intensity, the process comprising:
- suspending a crystalline polymorph A of (3R,5S)-7-[2-cyclopropyl-4-(4-fluorophenyl)quinolin-3-yl]-3,5-dihydroxy-6(E)-heptenoic acid hemicalcium salt in absolute ethanol;
- isolating the crystalline polymorph D; and
- exposing the isolated crystalline polymorph D to an atmosphere with a relative air humidity of 5 to 100%;
- wherein the crystalline polymorph A exhibits a characteristic X-ray powder diffraction pattern with characteristic peaks expressed in 2θ at 5.0 (s), 6.8 (s), 9.1 (s), 10.0 (w), 10.5 (m), 11.0 (m), 13.3 (vw), 13.7 (s), 14.0 (w), 14.7 (w), 15.9 (vw), 16.9 (w), 17.1 (vw), 18.4 (m), 19.1 (w), 20.8 (vs), 21.1 (m), 21.6 (m), 22.9 (m), 23.7 (m), 24.2 (s), 25.2 (w), 27.1 (m), 29.6 (vw), 30.2 (w), and 34.0 (w), wherein (vs) stands for very strong intensity, (s) stands for strong intensity, (m) stands for medium intensity, (w) stands for weak intensity, and (vw) stands for very weak intensity.

14. The process of claim 13, wherein exposing the isolated crystalline polymorph D to the atmosphere with the relative air humidity of 5 to 100%, comprises exposing the isolated crystalline polymorph D to an inert gas stream with a relative air humidity of 5 to 100%.

15. The process of claim 13, wherein the atmosphere has a relative air humidity of 40 to 80%.

16. A process for preparing a crystalline polymorph E of (3R,5S)-7-[2-cyclopropyl-4-(4-fluorophenyl)quinolin-3-yl]-3,5-dihydroxy-6(E)-heptenoic acid hemicalcium salt, which exhibits a characteristic X-ray powder diffraction pattern with characteristic peaks expressed in 2θ at 4.4 (vw), 5.0 (s), 6.6 (s), 6.8 (s), 8.9 (s), 10.0 (m), 10.3 (s), 10.8 (m), 13.3 (s), 13.6 (m), 14.0 (s), 15.2 (vw), 15.9 (w), 16.4 (w), 16.9 (vw), 17.8 (vw), 18.3 (m), 18.9 (w), 20.2 (vs), 20.4 (m), 20.7 (m), 20.9 (m), 21.1 (vs), 21.6 (m), 21.7 (m), 22.3 (m), 23.5 (m), 23.8 (m), 24.1 (w), 24.7 (vw), 25.4 (vw), 26.6 (m), 30.2 (w), and 34.0 (vw), wherein (vs) stands for very strong intensity, (s) stands for strong intensity, (m) stands for medium intensity, (w) stands for weak intensity, and (vw) stands for very weak intensity, the process comprising:
- suspending a crystalline polymorph A of (3R,5S)-7-[2-cyclopropyl-4-(4-fluorophenyl)quinolin-3-yl]-3,5-dihydroxy-6(E)-heptenoic acid hemicalcium salt in 1,4-dioxane containing water as a cosolvent;
- isolating the crystalline polymorph E; and
- exposing the isolated crystalline polymorph E to an atmosphere with a relative air humidity of 5 to 100%;
- wherein the crystalline polymorph A exhibits a characteristic X-ray powder diffraction pattern with characteristic peaks expressed in 2θ at 5.0 (s), 6.8 (s), 9.1 (s), 10.0 (w), 10.5 (m), 11.0 (m), 13.3 (vw), 13.7 (s), 14.0 (w), 14.7 (w), 15.9 (vw), 16.9 (w), 17.1 (vw), 18.4 (m), 19.1 (w), 20.8 (vs), 21.1 (m), 21.6 (m), 22.9 (m), 23.7 (m), 24.2 (s), 25.2 (w), 27.1 (m), 29.6 (vw), 30.2 (w), and 34.0 (w), wherein (vs) stands for very strong intensity, (s) stands for strong intensity, (m) stands for medium intensity, (w) stands for weak intensity, and (vw) stands for very weak intensity.

17. The process of claim 16, wherein exposing the isolated crystalline polymorph E to the atmosphere with the relative air humidity of 5 to 100%, comprises exposing the isolated crystalline polymorph E to an inert gas stream with a relative air humidity of 5 to 100%.

18. The process of claim 16, wherein the atmosphere has a relative air humidity of 40 to 80%.

19. A process for preparing a crystalline polymorph E of (3R,5S)-7-[2-cyclopropyl-4-(4-fluorophenyl)quinolin-3-yl]-3,5-dihydroxy-6(E)-heptenoic acid hemicalcium salt, which exhibits a characteristic X-ray powder diffraction pattern with characteristic peaks expressed in 2θ at 4.4 (vw), 5.0 (s), 6.6 (s), 6.8 (s), 8.9 (s), 10.0 (m), 10.3 (s), 10.8 (m), 13.3 (s), 13.6 (m), 14.0 (s), 15.2 (vw), 15.9 (w), 16.4 (w), 16.9 (vw), 17.8 (vw), 18.3 (m), 18.9 (w), 20.2 (vs), 20.4 (m), 20.7 (m), 20.9 (m), 21.1 (vs), 21.6 (m), 21.7 (m), 22.3 (m), 23.5 (m), 23.8 (m), 24.1 (w), 24.7 (vw), 25.4 (vw), 26.6 (m), 30.2 (w), and 34.0 (vw), wherein (vs) stands for very strong intensity, (s) stands for strong intensity, (m) stands for medium intensity, (w) stands for weak intensity, and (vw) stands for very weak intensity, the process comprising:
- suspending a crystalline polymorph A of (3R,5S)-7-[2-cyclopropyl-4-(4-fluorophenyl)quinolin-3-yl]-3,5-dihydroxy-6(E)-heptenoic acid hemicalcium salt in methanol containing water as a cosolvent;
- isolating the crystalline polymorph E; and
- exposing the isolated crystalline polymorph E to an atmosphere with a relative air humidity of 5 to 100%;
- wherein the crystalline polymorph A exhibits a characteristic X-ray powder diffraction pattern with characteristic peaks expressed in 2θ at 5.0 (s), 6.8 (s), 9.1 (s), 10.0 (w), 10.5 (m), 11.0 (m), 13.3 (vw), 13.7 (s), 14.0 (w), 14.7 (w), 15.9 (vw), 16.9 (w), 17.1 (vw), 18.4 (m), 19.1 (w), 20.8 (vs), 21.1 (m), 21.6 (m), 22.9 (m), 23.7 (m), 24.2 (s), 25.2 (w), 27.1 (m), 29.6 (vw), 30.2 (w), and 34.0 (w), wherein (vs) stands for very strong intensity, (s) stands for strong intensity, (m) stands for medium intensity, (w) stands for weak intensity, and (vw) stands for very weak intensity.

20. The process of claim 19, wherein exposing the isolated crystalline polymorph E to the atmosphere with the relative air humidity of 5 to 100%, comprises exposing the isolated crystalline polymorph E to an inert gas stream with a relative air humidity of 5 to 100%.

21. The process of claim 19, wherein the atmosphere has a relative air humidity of 40 to 80%.

22. A process for preparing a crystalline polymorph F of (3R,5S)-7-[2-cyclopropyl-4-(4-fluorophenyl)quinolin-3-yl]-3,5-dihydroxy-6(E)-heptenoic acid hemicalcium salt, which exhibits a characteristic X-ray powder diffraction pattern with characteristic peaks expressed in 2θ at 5.1 (m), 5.6 (w), 7.0 (s), 8.8 (m), 9.6 (s), 10.2 (w), 10.9 (m), 11.3 (w), 11.9 (m), 12.5 (m), 13.0 (s), 13.7 (m), 14.4 (s), 14.7 (m), 15.3 (vw), 15.5 (w), 16.8 (m), 17.6 (w), 18.3 (m), 19.3 (m), 19.7 (m), 20.6 (m), 21.2 (vs), 21.8 (s), 22.8 (s), 23.1 (w), 23.8 (w, shoulder), 24.1 (s), 24.8 (s), 25.7 (m), 26.2 (vw), 26.6 (m), 26.9 (w), 28.4 (w), 29.5 (w), 29.8 (vw), and 30.9 (m), wherein (vs) stands for very strong intensity, (s) stands for strong intensity, (m) stands for medium intensity, (w) stands for weak intensity, and (vw) stands for very weak intensity, the process comprising:
- suspending the crystalline polymorph A of (3R,5S)-7-[2-cyclopropyl-4-(4-fluorophenyl)quinolin-3-yl]-3,5-dihydroxy-6(E)-heptenoic acid hemicalcium salt in methanol containing water as a cosolvent;
- isolating the crystalline polymorph F; and
- exposing the isolated crystalline polymorph F to an atmosphere with a relative air humidity of 5 to 100%;

wherein the crystalline polymorph A exhibits a characteristic X-ray powder diffraction pattern with characteristic peaks expressed in 2θ at 5.0 (s), 6.8 (s), 9.1 (s), 10.0 (w), 10.5 (m), 11.0 (m), 13.3 (vw), 13.7 (s), 14.0 (w), 14.7 (w), 15.9 (vw), 16.9 (w), 17.1 (vw), 18.4 (m), 19.1 (w), 20.8 (vs), 21.1 (m), 21.6 (m), 22.9 (m), 23.7 (m), 24.2 (s), 25.2 (w), 27.1 (m), 29.6 (vw), 30.2 (w), and 34.0 (w), wherein (vs) stands for very strong intensity, (s) stands for strong intensity, (m) stands for medium intensity, (w) stands for weak intensity, and (vw) stands for very weak intensity.

23. The process of claim 22, wherein exposing the isolated crystalline polymorph F to the atmosphere with the relative air humidity of 5 to 100%, comprises exposing the isolated crystalline polymorph F to an inert gas stream with a relative air humidity of 5 to 100%.

24. The process of claim 22, wherein the atmosphere has a relative air humidity of 40 to 80%.

25. A process for preparing the amorphous form of (3R,5S)-7-[2-cyclopropyl-4-(4-fluorophenyl)quinolin-3-yl]-3,5-dihydroxy-6(E)-heptenoic acid hemicalcium salt, the process comprising:
   adding a non-solvent to a solution of (3R,5S)-7-[2-cyclopropyl-4-(4-fluorophenyl)quinolin-3-yl]-3,5-dihydroxy-6(E)-heptenoic acid hemicalcium salt in an organic solvent;
   isolating the amorphous form; and
   exposing the isolated amorphous form to an atmosphere with a relative air humidity of 5 to 100%.

26. The process of claim 25, wherein exposing the isolated amorphous form to the atmosphere with the relative air humidity of 5 to 100%, comprises exposing the isolated amorphous form to an inert gas stream with a relative air humidity of 5 to 100%.

27. The process of claim 25, wherein the atmosphere has a relative air humidity of 40 to 80%.

28. A process for preparing the amorphous form of (3R,5S)-7-[2-cyclopropyl-4-(4-fluorophenyl)quinolin-3-yl]-3,5-dihydroxy-6(E)-heptenoic acid hemicalcium salt, the process comprising:
   drying an aqueous solution of (3R,5S)-7-[2-cyclopropyl-4-(4-fluorophenyl)quinolin-3-yl]-3,5-dihydroxy-6(E)-heptenoic acid hemicalcium salt by lyophilization;
   isolating the amorphous form; and
   exposing the isolated amorphous form to an atmosphere with a relative air humidity of 5 to 100%.

29. The process of claim 28, wherein exposing the isolated amorphous form to the atmosphere with the relative air humidity of 5 to 100%, comprises exposing the isolated amorphous form to an inert gas stream with a relative air humidity of 5 to 100%.

30. The process of claim 28, wherein the atmosphere has a relative air humidity of 40 to 80%.

* * * * *